United States Patent
Zohar et al.

(10) Patent No.: US 7,194,978 B2
(45) Date of Patent: Mar. 27, 2007

(54) INDUCING STERILITY IN FISH BY DISRUPTING THE DEVELOPMENT OF THE GNRH SYSTEM

(75) Inventors: Yonathan Zohar, Baltimore, MD (US); Yoav Gothilf, Zichron Yaakov (IL); Susan Wray, Chevy Chase, MD (US)

(73) Assignees: University of Maryland Biotechnology Institute, Baltimore, MD (US); Ramot at Tel Aviv University (IL); United States of America, Washington, DC (US)

( * ) Notice: Subject to any disclaimer, the term of this patent is extended or adjusted under 35 U.S.C. 154(b) by 88 days.

(21) Appl. No.: 10/924,001

(22) Filed: Aug. 23, 2004

(65) Prior Publication Data

US 2005/0132969 A1 Jun. 23, 2005

Related U.S. Application Data

(60) Provisional application No. 60/497,101, filed on Aug. 22, 2003.

(51) Int. Cl.
*A01K 61/00* (2006.01)

(52) U.S. Cl. ...................... 119/217; 119/215

(58) Field of Classification Search ............. 119/217, 119/215, 227, 231, 233, 216, 218, 260, 259; 514/2, 15
See application file for complete search history.

(56) References Cited

U.S. PATENT DOCUMENTS 4,410,514 A * 10/1983 Vale et al. ................ 514/15
4,443,368 A * 4/1984 Sherwood et al. .......... 530/328
5,288,705 A    2/1994 Zohar
5,378,688 A * 1/1995 Nett et al. ................ 514/15
5,488,036 A * 1/1996 Nett et al. ................ 514/15
5,631,229 A * 5/1997 Nett et al. ................ 514/15
5,643,877 A * 7/1997 Zohar et al. .............. 514/15
5,786,457 A * 7/1998 Nett et al. ................ 530/402
6,103,881 A * 8/2000 Nett et al. ................ 530/402
6,210,927 B1 * 4/2001 Zohar et al. .............. 435/69.4
6,443,097 B1   9/2002 Zohar et al.
6,489,458 B2 * 12/2002 Hackett et al. ........... 536/23.2
6,635,740 B1 * 10/2003 Enright et al. ............ 530/324
6,949,365 B2 * 9/2005 Sower et al. ............. 435/69.4
2002/0013955 A1 * 1/2002 Ogden et al. .............. 800/20

(Continued)

FOREIGN PATENT DOCUMENTS

CA       2501624       * 10/2005

OTHER PUBLICATIONS

Arai, Katsutoshi, Genetic improvement of aquaculture finfish species by chromosome manipulation techniques in Japan, *Aquaculture*, vol. 197 (2001) 205-228.

(Continued)

*Primary Examiner*—Yvonne R. Abbott
(74) *Attorney, Agent, or Firm*—Steven J. Hultquist; Intellectual Property/Technology Law

(57) ABSTRACT

The present invention provides for a method for inducing sterility in fish by administering at least one compound that disrupts the establishment of the gonadotropin-releasing hormone system during early development thereby inhibiting sexual maturity in the treated fish. Effective compounds include GABA, GABA receptor agonists, or GABA receptor antagonists.

18 Claims, 6 Drawing Sheets

U.S. PATENT DOCUMENTS

2002/0165126 A1* 11/2002 Nett et al. .................... 514/2

OTHER PUBLICATIONS

Benfey, Tillmann J., et al., Growth and Gonadal Development in Triploid Landlocked Atlantic Salmon (*Salmo salar*), *Can. J. Fish. Aquat. Sci.* vol. 41 (1984) 1387-1392.

Bless, Elizabeth P., et al., Effects of γ-Aminobutyric Acid$_A$ Receptor Manipulation on Migrating Gonadotropin-Releasing Hormone Neurons through the Entire Migratory Route *in Vivo* and *in Vitro*, *Endocrinology*, vol. 141 (2000) 1254-1262.

Braat, Arie Koen, et al., Characterization of Zebrafish Primordial Germ Cells: Morphology and Early Distribution of vasa RNA, *Developmental Dynamics*, vol. 216 (1999) 153-167.

Carr, J.W., et al., The occurrence and spawning of cultured Atlantic salmon (*Salmo salar*) in a Canadian river, *ICES Journal of Marine Science*, vol. 54 (1997) 1064-1073.

Galbreath, Peter F., et al., Sexual maturation and fertility of diploid and triploid Atlantic salmon×brown trout hybrids, *Aquaculture*, vol. 137 (1995) 299-311.

Johnstone, R., Maturity control in Atlantic salmon, *Recent Advances in Aquaculture*, (J.F. Muir & R.J. Roberts, eds. ) pp. 99-105, Blackwell Scientific Publications, London.

Knibb, W., Genetic improvement of marine fish—which method for industry? *Aquaculture Research*, vol. 31 (2000) 11-23.

Naylor, Rosamond L., et al., Nature's Subsidies to Shrimp and Salmon Farming, *Science*, vol. 282 (1998) 883-884.

Parhar, I.S., et al., Regulation of forebrain and midbrain GnRH neurons in juvenile teleosts, *Fish Physiology and Biochemistry*, vol. 17 (1997) 81-84.

Pauly, Daniel, et al., Primary production required to sustain global fisheries, *Nature*, vol. 374 (1995) 255-257.

Pauly, Daniel, et al., Fishing Down Marine Food Webs, *Science*, vol. 279 (1998) 860-863.

Piferrer, F, et al., Sex Control in Pacific Salmon, *Recent Advances in Aquaculture*, (J.F. Muir & R.J. Roberts, eds. ) pp. 99-106, Blackwell Scientific Publications, London 69-77.

Safina, Carl, The World's Imperiled Fish, *Scientific American Presents*, (1998) 58-63.

The Promise and Perils of Aquaculture, *Scientific American Presents*, (1998) 64-69.

Volpe, et al., Reproduction of aquacultured Atlantic Salmon in Canadian Rivers, *Transactions of the American Fisheries Society*, vol. 130 (2001) 489-494.

White, Richard B., et al., Ontogeny of Gonadotropin-Releasing Hormone (GnRH) Gene Expression Reveals a Distinct Origin for GnRH-Containing Neurons in the Midbrain, *General and Comparative Endocrinology*, vol. 112 (1998) 322-329.

Wong, Ten-Tsao, et al., Developmental Expression of Three Forms of Gonadotropin-Releasing Hormone and Ontogeny of the Hypothalamic-Pituitary-Gonadal Axis in Gilthead Seabream (*Sparus aurata*), *Biology of Reproduction*, vol. 71 (2004) 1026-1035.

Zohar, Yonathan, et al., Endocrine manipulations of spawning in cultured fish: from hormones to genes, *Aquaculture*, vol. 197 (2001) 99-136.

* cited by examiner

INDUCING STERILITY IN FISH BY DISRUPTING THE DEVELOPMENT OF THE GNRH SYSTEM

CROSS-REFERENCE TO RELATED APPLICATIONS

This application claims priority from U.S. Provisional Patent Application No. 60/497,101 filed on Aug. 22, 2003 in the names of Yonathan Zohar, Yoav Gothilf and Susan Wray for "INDUCING STERILITY IN FISH BY DISRUPTING THE DEVELOPMENT OF THE GnRH SYSTEM" the contents of which are incorporated by reference herein for all purposes.

BACKGROUND OF THE INVENTION

1. Technical Field

The present invention relates generally to methods of producing sterile fish, and more particularly, to method of inducing sterility in fish by altering developmental migration of gonadotropin-releasing hormone (GnRH) neurons.

2. Description of Related Art

In recent years the world has witnessed an alarming decline in commercial fisheries, the result of over fishing of wild fisheries stocks and indirectly, the failure of commercial aquaculture to reduce demand for fisheries products (i.e., by a sufficient increase in commercially farmed fish products). According to the Food and Agriculture Organization (FAO) of the United Nations, nearly 70% of the world's commercial marine fisheries species are now fully exploited, overexploited or depleted. Based on anticipated population growth, it is estimated that the world's demand for seafood will double by the year 2025. Therefore, a growing gap is developing between demand and supply of fisheries products, which results in a growing seafood deficit. Even the most favorable estimates project that in the year 2025 the global demand for seafood will be twice as much as the commercial fisheries will harvest.

The same trend exists in the United States marketplace. Per capita seafood consumption is on the rise, but United States seafood harvests are not increasing to meet the demand. Moreover, only 10% of the seafood consumed in the United States comes from domestic aquaculture and the United States ranks only tenth in the world in the value of its aquaculture production. As a result, the United States is overwhelmingly dependent on imported seafood, such as gilthead, seabream, with more than half of its supplies coming from overseas.

Worldwide, it is estimated that in order to close the increasing gap between demand and supplies of fisheries product, aquaculture will need to augment production fivefold during the next two and half decades. While there is a need to increase global and United States aquaculture production, it is clear that fish farming must develop as a sustainable industry without having an adverse impact on the environment.

In commercial fish species where sexual maturation occurs before the fish has reached market size, energy is spent on gonadal growth instead of muscle growth. Sterility increases the conversion of food energy to muscle (thereby resulting in larger fish fillets) and minimizes food energy diverted for development of the gonads. However current method of fish sterilization carries environmental issues, such as escape of cultured fish possess that may threaten the ecological imbalance or genetic contamination of wild populations. This threat will become even greater as transgenic fish are raised in commercial operations in the United States and abroad.

Aquaculture experts around the world agree that a mechanically simple, but effective, process that bypasses the traditional modes of inducing sterility would increase production efficiency, profitability and biosecurity in commercial aquaculture. Sterilizing transgenic or genetically-selected fish will minimize the possibility of potential aquacultured escapees propagating in the wild, especially in light of alarming reports of interbreeding between escaped animals and wild populations of the same species seem to be increasing in areas of intensive farming (Volpe et al., 2001; Carr et al., 1997).

Several methods currently exist that are used to induce sterility in fish. Chromosome set manipulation for the production of triploid sterile populations is used but it is a cumbersome procedure that must be individually developed for each species. Furthermore, generation of triploids does not always result in sterility. In induced-triploid rainbow trout (Arai, 2001) and Atlantic salmon (Donaldson and Benfey, 1987), males were seldom completely sterile. Because they maintain most of their endocrine competence, these salmonids also exhibit secondary sex characteristics, and as a consequence are susceptible to disease and exhibit no improvement in growth over diploids. Likewise, female triploid Atlantic salmon are commonly found to have a few normal oocytes within the ovarian matrix (Johnstone, 1993). Like CSM, inter-hybridization (or hybrid production) is a labor-intensive process that does not always result in sterility, as is clearly the case with the hybrid striped bass.

As a result of the above constraints, the production of sterile fish, although considered highly beneficial to commercial aquaculture, has not yet been developed for mass use in the industry. Thus, it would be advantageous to develop a method and system to induce permanent sterility in fish grown in commercial operations that overcome the problems of the previous complex and unsuccessful methods used for sterilization.

SUMMARY OF THE INVENTION

The present invention relates to a simple and generic technology for inducing sterility in farmed fish which completely and permanently disrupt gonadal development by altering the establishment of the gonadotropin-releasing hormone thereby creating fish having more muscle (desirable tissue) and less gonad (undesirable tissue).

In one aspect the present invention relates to a method of sterilizing fish comprising disrupting the establishment of the gonadotropin-releasing hormone system during early development.

In another aspect, the present invention provides for a method for inducing sterility in fish, the method comprising: administering at least one compound that disrupts the establishment of the gonadotropin-releasing hormone system during early development.

In yet another aspect, the present invention provides for a method to permanently sterilize a fish, the method comprising:

administering to fish larvae GABA, GABA receptor agonist, or GABA receptor antagonist in an effective amount to disrupt the establishment of the gonadotropin-releasing hormone system thereby permanently sterilizing the mature fish.

Preferably, GABA, a GABA receptor agonist, or a GABA receptor antagonist is administered by injection, implantation, dissolving in water wherein the fish are swimming or orally through feed.

Yet another aspect of the present invention relates to a method of sterilizing fish comprising:

contacting an embryonic or juvenile fish that is sexually immature with gamma aminobutyric acid or a functional analog or equivalent thereof in an effective amount to disrupt the establishment of the gonadotropin-releasing hormone system during early development thereby inhibiting sexual maturity.

The GABA functional analog or equivalent thereof may be selected from the group including aminovaleric acid; 3-amino-4-cyclopentane-1-carboxylic acid; muscimol; baclofen, bicuculline; diazepam; topiramate, beta-p-chlorophenyl-GABA; dehydroepiandrosterone, Netrins, nasal embryonic LHRH factor or compounds with similar disruptive effects on the development of the GnRH system.

Another aspect of the present invention relates to a kit for distributing compounds that inhibit the establishment of the GnRH system in fish and instructions to effectively sterilize fish.

Other aspects and features of the invention will be more fully apparent from the ensuing disclosure and appended claims.

DETAILED DESCRIPTION OF THE INVENTION

Figure 1:
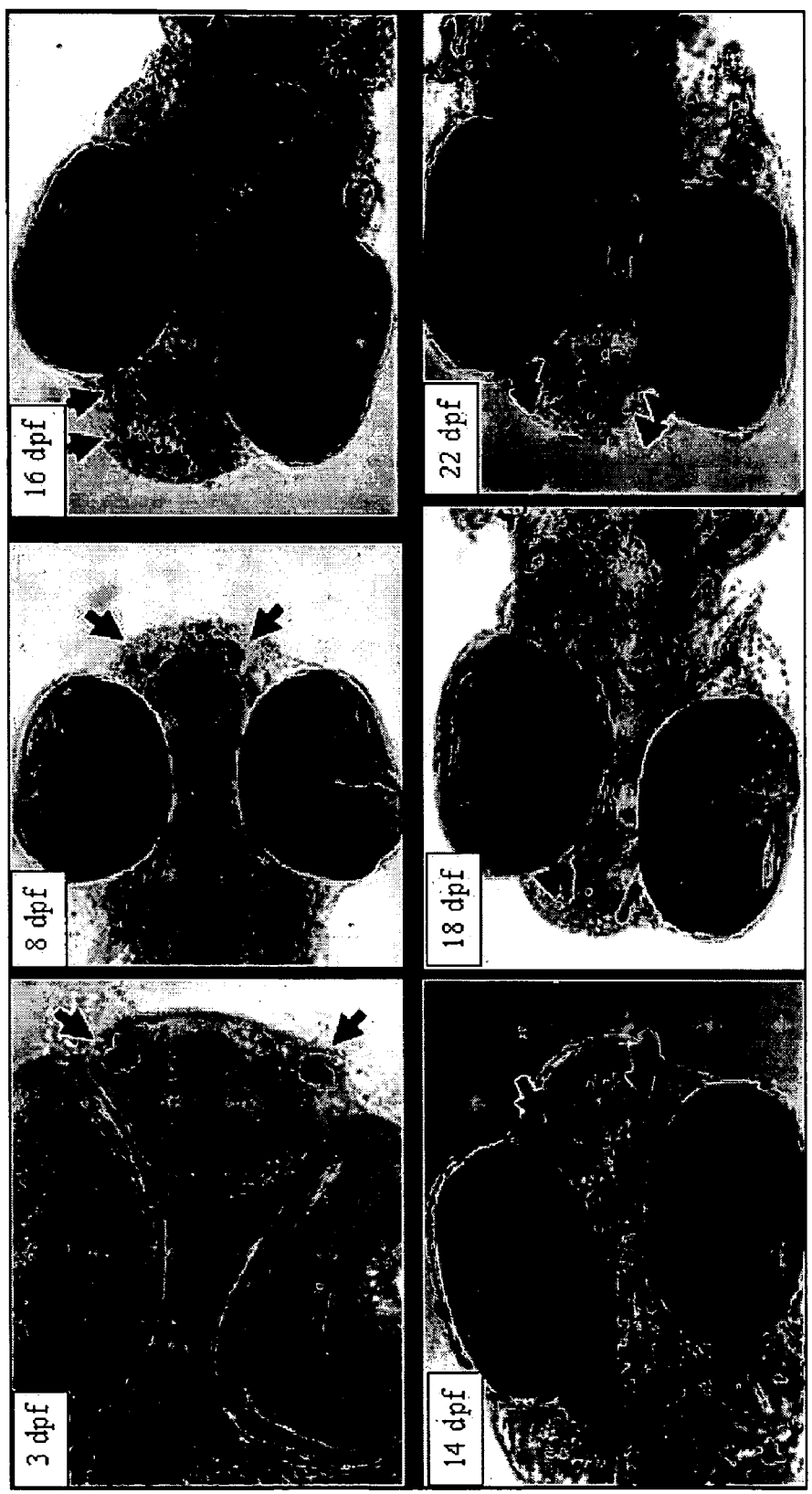
FIG. 1 shows the developmental migration of TN GnRH neurons in the gilthead seabream. Digoxigenin (DIG)-labeled complimentary RNA (cRNA) probe was synthesized from plasmid DNA, containing the seabream TN GnRH cDNA, using T7 RNA polymerase. The probe was hybridized to cellular TN GnRH mRNA in whole, fixed 3–22 days pf of larvae. The hybridized probe was then detected with anti-DIG antibody conjugated to alkaline phosphatase (Anti-DIG-AP), and the complex (mRNA:DIG-labeled cRNA:Anti-DIG-AP) was detected by an enzymatic reaction of AP with a chromogenic substrate, which forms a precipitating dark purple pigment. The procedure was performed according to a standard published protocol for whole-mount ISH (Westerfield et al., 1995). The age of the larvae are boxed on the top left of each photograph. TN GnRH-expressing cells are indicated by an arrow.

The present invention is an innovative, simple and generic technology for inducing sterility in farmed fish. This technology aims to completely and permanently disrupt gonadal development by specifically altering the establishment of the key hormonal system responsible for sexual maturation, that of the gonadotropin-releasing hormone. The phenotypic result of this technology is a market-sized fish that has more muscle (desirable tissue) and less gonad (undesirable tissue). An additional component of this technology is that it minimizes the potential adverse genetic effects of aquaculture on the environment (i.e., the escape and breeding of farmed fish), thereby making this a very environmentally friendly technology.

As defined herein, "sterilizing" fish is understood to mean making a fish unable to sexually reproduce. Sterile fish are defined as fish that are unable to reproduce when reaching sexual maturity.

As defined herein, "fish" means any commercially farmed fish species, either freshwater or saltwater species, including, without limitation, gilthead seabream (*Sparus aurata*), haddock, reedfish (*Calamoichthys calabaricus*), sturgeon (*Acipenser transmontanus*), snook (*Centropomus undecimalis*), black sea bass (*Centropristis striata*), masu salmon, Atlantic salmon, rainbow trout, monkfish, sole, perch, grouper, catfish, blue gill, yellow perch, white perch, sunfish, tilapia, flounder, mahi mahi, striped bass, shad, pike, whitefish, swordfish, red snapper, baramundi, turbot, red drum, as well as ornamental species such as zebrafish.

As defined herein, "functional equivalent" means that the compound retains some or all of the biological activity of the corresponding compound.

The term "functional analog," as used herein means compounds derived from a particular parent compound by straightforward substitutions that do not result in a substantial (i.e. more than 100×) loss in the biological activity of the parent compound, where such substitutions are modifications well-known to those skilled in the art.

Described herein is a process for inducing sterility in commercially important marine species by administering a substance that disrupts the establishment of the gonadotropin-releasing hormone system during early development. In one embodiment, the process involves introducing into the system of an embryonic or juvenile fish a compound that alters the early establishment of the GnRH system, thereby altering the neuronal migration and establishment of the gonadotropin-releasing hormone (GnRH) system. Preferably the process includes the introduction of gammaminobutyric acid (GABA), compounds have similar functionality, analogues, a GABA receptor agonist, GABA receptor antagonist or other compounds exhibiting similar functionality.

Gamma-aminobutyric acid, commonly known as GABA, is an amino acid derivative, which serves as one of the major neurotransmitters in a fish central nervous system, particularly the brain. GABA is a well-known inhibitor of presynaptic transmission in the CNS, and also in the retina. The formation of GABA occurs by the decarboxylation of glutamate catalyzed by glutamate decarboxylase (GAD). GABA exerts its effects by binding to two distinct receptors, GABA-A and GABA-B.

In general, neurotransmitters are responsible for regulating the conductance of ions across neuronal membranes. The profound influence of GABA on the central nervous system is related to the presence of GABA receptors in up to 40% of the neurons in the brain alone. GABA regulates the excitability of individual neurons by regulating the conductance of ions across the neuronal membrane. For example, GABA interacts with its recognition site on $GABA_A$ receptors, resulting in an increase in membrane permeability to chloride ions that render the neuron less susceptible to further stimulation.

The GnRH system is the pivotal hormonal system in the reproductive hormone axis of vertebrates. In most fish species, multiple forms of GnRH, a decapeptide hormone, are present. Hypothalamic GnRH-producing neurons have a distinctive embryonic development. They originate from the nasal placode, migrate along olfactory axons into the forebrain, and continue to the preoptic area and hypothalamus where they function to stimulate gonadotropin secretion from the pituitary gland. In mammals, an appropriate location of GnRH neurons within the hypothalamus is necessary for normal reproductive function in the adult; abnormal migration and targeting of GnRH neurons during embryogenesis results in hypogonadism and infertility. The developmental migration of GnRH neurons in mammals is modulated, in part, by GABA input; GnRH neuronal migration and entrance into the forebrain is inhibited by GABAergic activation.

The Invention:

GnRH System Inhibitor

The compositions of the present invention may include any compound that inhibits the establishment of the gonadotropin-releasing hormone system. The compound may include, without limitation, GABA and compounds having similar functionality including aminovaleric acid; 3-amino-4-cyclopentane-1-carboxylic acid; muscimol; baclofen, bicuculline; diazepam; topiramate, beta-p-chlorophenyl-GABA; dehydroepiandrosterone, or compounds with similar disruptive effects on the development of the GnRH system.

Routes of Administration and Dosage Forms

The compositions according to the present invention, may be administered by any suitable route including injection, implantation, immersing the embryonic or juvenile fish in a bath of an effective substance or through a feed product. For example, and not by way of limitation, the active ingredient may be directly injected intramuscularly into the fish. In one embodiment, the active compound may be combined with a polymer based carrier matrix into a sustained release delivery system.

The term "sustained release" is understood to mean a gradual release of the active compound in a controlled manner. A suitable carrier having such sustained release properties may be chosen on the basis of its gradual release properties in a solution designed to resemble a fish's plasma, such as a ringer solution, other physiological saline solutions, fish serum, etc.

The polymer based carrier matrix may comprise natural or synthetic polymers or copolymers. Examples of natural polymers are polysaccharides and various proteins. Synthetic polymers or copolymers may either be biodegradable, in which case the sustained release is due to biodegradation, or non degradable, in which case the sustained release is due to gradual diffusion of the active compound therefrom. Examples of biodegradable polymers and copolymers are polylactic polyglycolic acid, polyanhydrides, polyorthoesters and polycaprolactone. Examples of non biodegradable polymers are silicone rubber in a mixture with a relatively large amount of a biocompatible protein, a copolymer of ethylene and vinyl acetate, the relative amount of vinyl acetate being about 20–50%, and various synthetic polysaccharides. In general, any biocompatible polymeric controlled release carrier such as those hitherto used in the art for delivering the GnRH system inhibitor compounds, may in principle be used in accordance with the present invention.

The compositions of the present invention, if delivered in a solid form, may be prepared in any suitable form such as pellets, discs, rods or microspheres. These may be administered to the fish larvae either by implantation of a composition unit (in the form of a pellet, disc or rod) or by injection, either intramuscular, subcutaneous or intraperitoneal (in the form of a suspension of mini-rods or microspheres).

The size of an implantable composition in accordance with the present invention will be determined both by the size of the fish in which implantation thereof is intended, i.e. it should not be too big, and by practical limitations, i.e. the implantable composition should not be too small so as to render it difficult for manipulation. Thus, for example, a disc having a diameter of about 1–10 mm and a thickness of about 0.01–2 mm has been found to be suitable for implantation in many fish such as the sea bream, sea bass and trout.

The composition may be administered to the fish either by subcutaneous or intra-peritoneal implantation (for injectable micro-rods or spheres). For subcutaneous implantation a small incision are made through the fish's skin at a suitable place and after separating the skin from the underlying muscles, e.g., by the use of forceps, the implantation and incision is made through the skin and muscle of the peritoneal cavity and the implant is inserted through the incision and placed in the peritoneum. The incision in each case is made as small as practicably possible and there is usually no need for post implantational stitching.

Injectable compositions in accordance with the invention in the form of mini-rods or microspheres should be sufficiently small to pass through a syringe. Injectable compositions will be suspended in an injectable solution, such as saline or various buffers, prior to injection. and thereafter the suspension is injected into a suitable muscle of the fish or into the peritoneal cavity.

Implantable compositions may preferably comprise about 300 ug of the active compounds per unit. When administering an injectable composition in accordance with the invention, the administered composition will preferably comprise about 5–200 ug of the active compound per kg of body weight of the injected fish. The amount of the active compound may, in some cases, be reduced if a very active analog is utilized.

Further and preferably for embryonic fish or larvae, the GnRH system inhibiting compounds can simply be added to fish feed or water system, either freshwater or saltwater, in various concentrations, as described herein. Additionally, the fish may be subjected to the compound by "dipping" the fish therein. The compound may be fused to a modulator, e.g., organic polycations that adhere to the skin and gills of the fish, thereby transferring the GnRH system inhibiting compounds to the fish.

The exposure of the fish to the GnRH system inhibiting compound can include intermittent (e.g., interrupted) as well as continuous (e.g., non-interrupted) exposure. The dose of the GnRH system inhibiting compound that is effective for inhibiting the establishment of the GnRH system can be routinely determined by a veterinarian, although it may vary depending on the species of fish treated, and the age of the fish. The treatment is administered daily, for a period of 1 to 14 days and preferably for 2 to 7 days. It has been surprisingly discovered that GABA and functional equivalents thereof caused a permanent sterility in the treated fish.

A kit in accordance with the present invention may be in any form suitable for providing a supply of GABA or its functional equivalent up to about 7 days, together with written instructions for administering it according to the dosing levels and schedule described above. Examples include, but are not limited to, various containers (e.g., bottles, cartons, blister packs, and ampules) either accompanied by a package insert describing the cyclical dosing instructions, or wherein the dosing instructions are printed on, or affixed to the container. The compound or its salt may be in the form of a pre-mix, comprising one or more diluents and 0.01 to 25% by weight of the compounds.

A treated fish feed may be prepared by incorporating a suitable amount of the GnRH system inhibiting compound into a commercially available fish feed products to achieve the desired dosing levels. The amount of incorporated into the fish feed will depend on the rate at which the fish are fed. For fish fed at the rate of 0.2% to 4% of biomass/day, the treated feed preferably contains from 0.5 to 100 mg of the compound per kg of treated feed, more preferably, from 1 to 50 mg per kg of treated feed, and most preferably, from 5 to 15 mg per kg of treated feed.

Preferably, the fish are raised in a recirculating aquaculture system, such as that described in U.S. Pat. No. 6,443,097, the contents of which are hereby incorporated by reference herein for all purposes. Generally, the system comprises an assembly of tanks each containing an aqueous medium for a specific stage of the aquaculture process (broodstock conditioning, spawning, egg incubation, larval rearing, nursery rearing, and grow-out), with ancillary solids removal filters, biofilters having associated active microbial communities, oxygen (or oxygen-containing gas) sources, and automatic control unit(s) for monitoring and control of oxygen, salinity, temperature, photoexposure, pH and carbon dioxide in respective tanks of the aquaculture process system. However, because the present invention provides for administration of an GnRH system inhibiting compound, the photoregime described in the aquaculture recirculating system does not have to be adjusted to reduce the gonadal development process. The aquaculture process system may also include optional ancillary facilities, such as ozonation/disinfection units, foam fractionation (foam breaker or defoaming) units, brine generator units, automatic feeder units, biopsy facilities, harvesting/packaging facilities, etc.

The invention having been fully described, aspects of it are illustrated by the following examples. However, these examples do not limit the invention, which is defined by the appended claims.

EXAMPLE 1

Fish embryos are obtained through natural and/or induced spawning of captive broodstocks (Zohar, et al., 1988: International patent #087982; Mylonas et al., 1996; Sullivan et al., 1997; Westerfield, 1993). Embryos are typically obtained from spawns of 3–4 females, pooled, and reared under appropriate species conditions. During exposure/treatment periods, embryos/larvae are kept in individual tanks/aquaria supplied with oxygen and water is changed daily. After treatments, larvae are moved to larval rearing systems and reared under standard conditions (e.g., for seabream, conditions such as those identified within Zohar et al., 2002 U.S. Pat. No. 6,443,097, the contents of which are incorporated by reference herein for all purposes.

General GABA Immersion Procedure

Larval fish are immersed for periods of 1–48 hours in a concentration ranging from $10^{-8}$ to $10^{-2}$ M of GABA, a GABA analog and/or a related GABA agonist or antagonist. Larval fish are treated using this process at varying life cycle stages for optimal sterilization. Similarly, the length of time of immersion and concentration of GABA or an analog can be varied for optimal sterilization of the fish.

Seabream. Seabream larvae at 3 days, 1 week and 2 weeks post fertilization (pf) are immersed in various, species-dependent concentrations of GABA, or a related GABA agonist or antagonist, for a period of 18 hours (200 larvae per treatment). Larvae are collected 24 hours after the treatments and are raised according to standard rearing conditions noted in Zohar, et al., 2002 U.S. Pat. No. 6,443,097. In vivo changes in fish development have been confirmed in seabream. At 24 hours post-treatment, transcript levels for each of the 3 GnRHs in seabream were determined using real-time, fluorescence-based quantitative RT-PCR assays. Similarly, assays to confirm in vivo treatment effects, prior to adulthood, could be incorporated into the methodology for industrial use of this technology.

Zebrafish. Zebrafish larvae 5–8 days post-fertilization (dpf) and 7–10 dpf were immersed in GABA (1 mM) or Muscimol (100 micromolar). Muscimol is a potent GABA agonist that acts specifically on $GABA_A$ receptor subtypes. Similar to the post-treatment assays conducted on seabream larvae, zebrafish tissue samples (n=12) were collected at 7, 9, 10, and 12 days pf and also after 9 weeks of growth for detection/analysis of GnRH neuron development and histological analysis of the gonads. The migration of the GnRH neurons and gonadal development were clearly inhibited by the GABA-ergic treatments. Confirmation is made to determine the effectiveness of the treatment prior to sexual maturation (or lack thereof).

EXAMPLE 2

The data obtained from our studies demonstrated that treatment of larval fish with GABA-ergic compounds resulted in altered GnRH gene expression during early development, altered developmental migration of GnRH neurons, and subsequent inhibition of gonadal development. With the exception of our research, no studies to date have examined the control of developmental migration of GnRH neurons in fish species for the purpose of inducing permanent sterility.

Developmental Information on the GnRH System in Seabream and Other Perciform Fish In gilthead seabream and other perciform species, 2 forms of GnRH [referred to respectively as salmon (s) GnRH and seabream (sb) GnRH] are expressed in the forebrain—the optic bulb/terminal nerve (OB/TN) GnRH neurons express sGnRH, and the preoptic area (POA) GnRH neurons express sbGnRH. As in all other vertebrates, midbrain GnRH neurons express chicken GnRH-II (cGnRH-II). PCR amplification of the 3 GnRH mRNAs at different stages of development indicates that the OB/TN GnRH is first expressed at 36 hours pf, midbrain GnRH a few hours later, and POA GnRH at 14 days pf, as shown in FIG. 1.

Whole-mount in situ hybridization (ISH) analysis of OB/TN GnRH neurons indicates that starting at 3 days pf these neurons are located in the olfactory placode. A visible migration towards the forebrain starts at 10–14 dpf. Studies on other perciform fish species in our laboratories, namely sea bass and white bass, have demonstrated similar patterns of GnRH expression, in terms of timing and location.

Effect of GABA on GnRH Gene Expression in Seabream

Seabream larvae at 3 days, 1 week and 2 weeks pf were immersed in various concentrations of GABA ($10^{-7}$ to $10^{-3}$ M) for a period of 18 hours (200 larvae per treatment). Larvae were collected 24 hours after the treatments and transcript levels for each of the 3 GnRHs were determined using real-time, fluorescence-based quantitative RT-PCR assays.

Figure 2A:
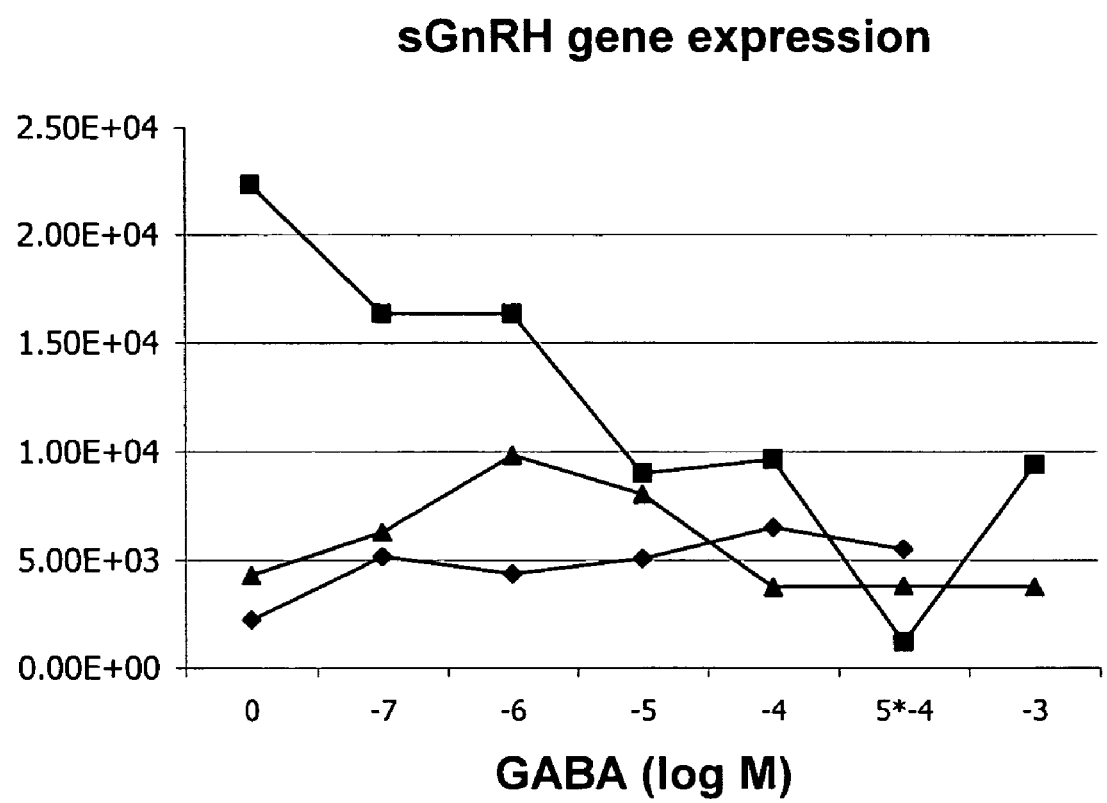
FIGS. 2A, B and C show the effect of GABA treatment on GnRH gene expression during development. Larvae were sampled 24 hours after overnight treatment at 3 days pf (-●-), 1 week pf (-■-) or 2 weeks pf (-◆-) and levels of GnRH transcript were measured by quantitative RT-PCR Values on the Y axis are expressed as copy number/20 ng total RNA. Values on the X axis range from 0 to 1 mM GABA. 100 ng total RNA was isolated from tissues using a modified acid-phenol extraction method (TRI REAGENT, MRC, Inc., Cincinnati, Ohio) and reverse transcribed into cDNA using random hexamers and MMLV reverse transcriptase. PCR was performed in 96-well plates on diluted cDNA templates using SYBR® Green PCR Core Reagent (PE Applied Biosystems, Foster City, Calif.) and the relevant GnRH primers. Primers were designed to span intron/exon boundaries in order to avoid amplification of genomic DNA. Amplification reactions were carried out using the ABI Prism® 7700 Sequence Detection System (PE Applied Biosystems), which consists of a built-in thermalcycler, laser irradiation and CCD detector system, and software analysis package. For each reaction, the Prism® 7700 generated an amplification plot of fluorescence signal versus cycle number, and $C_T$ (the fractional cycle number at which fluorescence passes a baseline threshold value) was determined (Fink et al., 1998). Standard curves were generated by plotting $C_T$ versus starting copy number for known amounts of template. Quantitation of the amount of target in each sample was accomplished by comparing $C_T$ values of unknowns to standards to determine initial copy number. Values were normalized to the amount of 18s RNA in each sample.
Figure 2B:
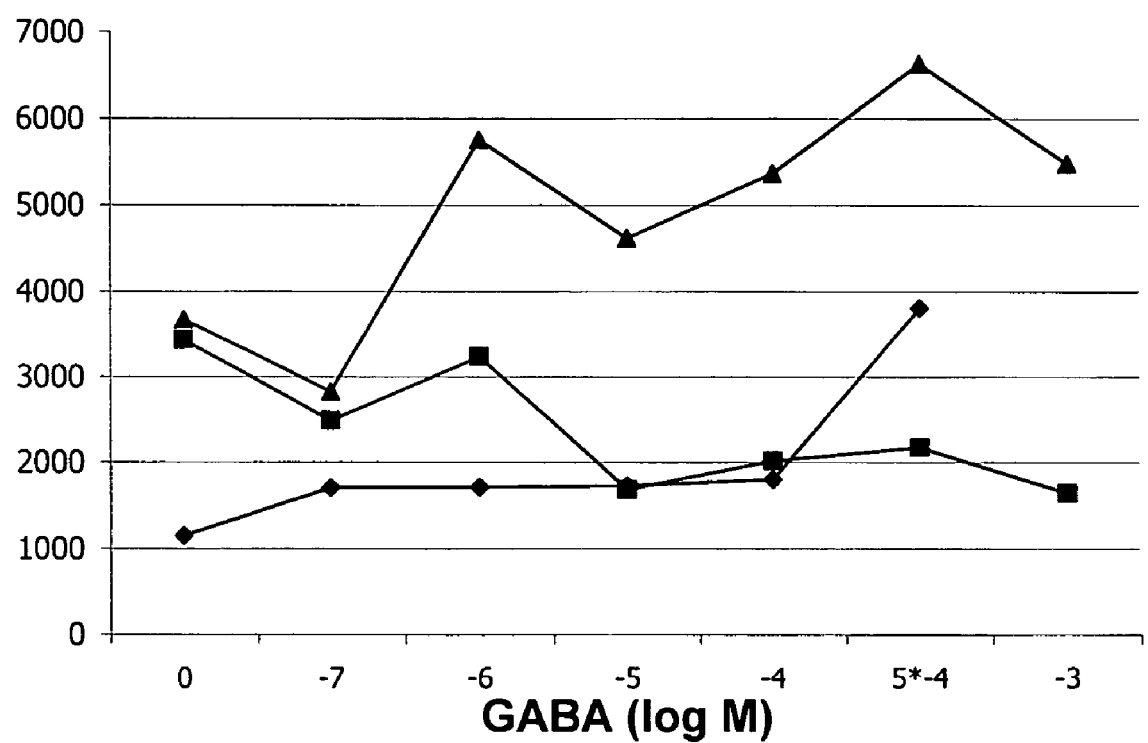
Figure 2C:
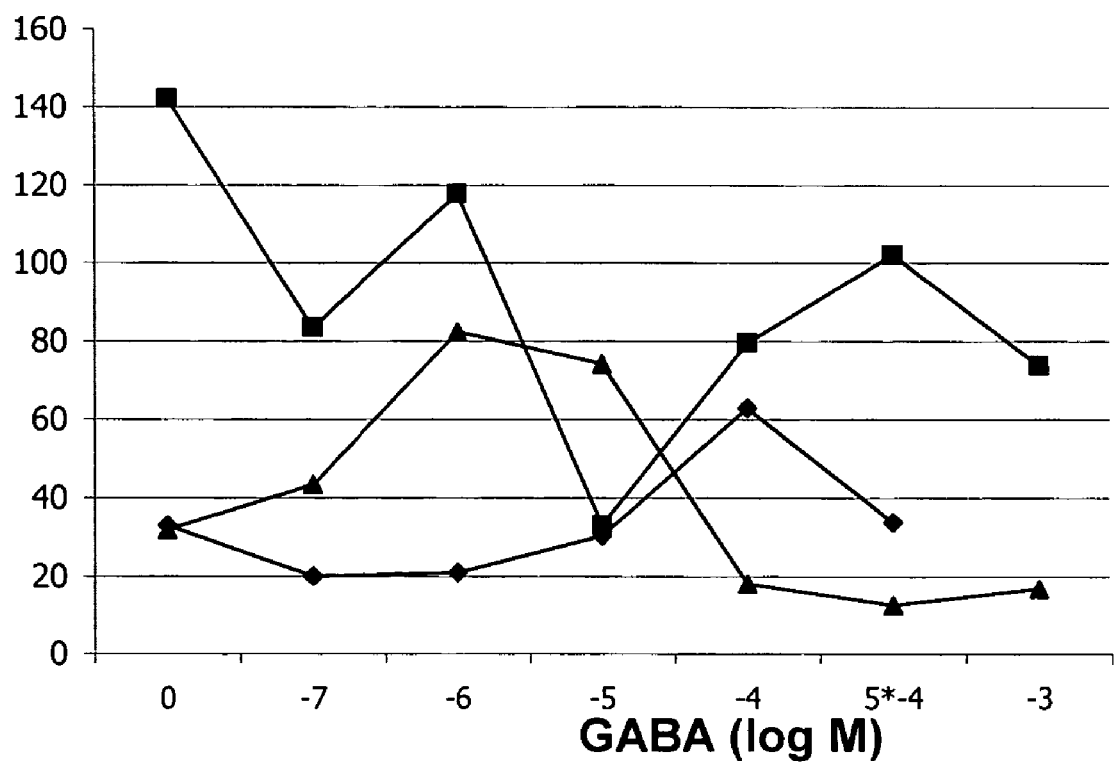

GABA treatment of 1-week-old larvae resulted in a dose-dependent decrease in sGnRH gene expression as shown in FIG. 2. GABA treatment in 3-day-old and 2-week-old larvae had no effect on sGnRH gene expression. Interestingly, a slight increase in cGnRH-II expression is seen with GABA treatment in 2-week-old larvae. The results for sbGnRH transcript levels are less clear, with no definitive effect seen. This is probably to be expected since in seabream, and other fish of the order Perciformes, significant sbGnRH expression has not been shown to occur in the brain until much later in development (Parhar et al., 1997; White and Fernald, 1998; Wong et al., 2000).

EXAMPLE 3

Effect of GABA on GnRH Neuronal Migration and Gonadal Development in Zebrafish

Zebrafish larvae were immersed in GABA (1 mM) or Muscimol (100 micromolar) at 5–8 days pf and 7–10 days pf. (Muscimol is a potent GABA agonist that acts specifically on $GABA_A$ receptor subtypes). Samples (n=12) were collected at 7, 9, 10, and 12 day pf for subsequent detection of GnRH neurons. The remaining fish were allowed to grow and, at 9 weeks, were sampled and processed for histological analysis of the gonads.

Figures 3A, 3B, 3C:
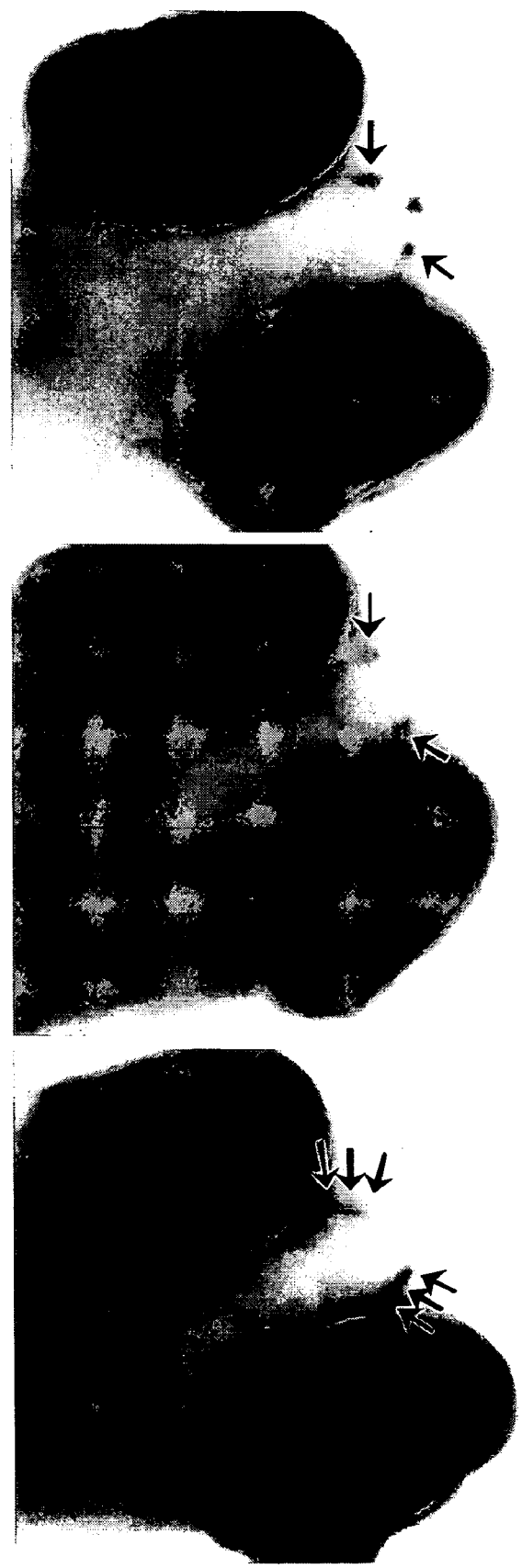
FIGS. 3A, B and C show the effect of GABA-ergic compounds on developmental migration of TN GnRH neurons in zebrafish. Whole-mount ISH analysis shows TN GnRH-expressing neurons in 12-day-old zebrafish larvae exposed to A) no treatment, B) 1 mM GABA, and C) 100 μM Muscimol. Note the extent of neuronal migration toward the brain seen in untreated fish, as compared to treated fish. Whole-mount ISH analysis was done as described in FIG. 1. Differential interference contrasting microscopy was used to visualize TN GnRH hybridization in deep tissue layers of the nasal placode. All panels at 200×.
Figures 4A, 4B, 4C:
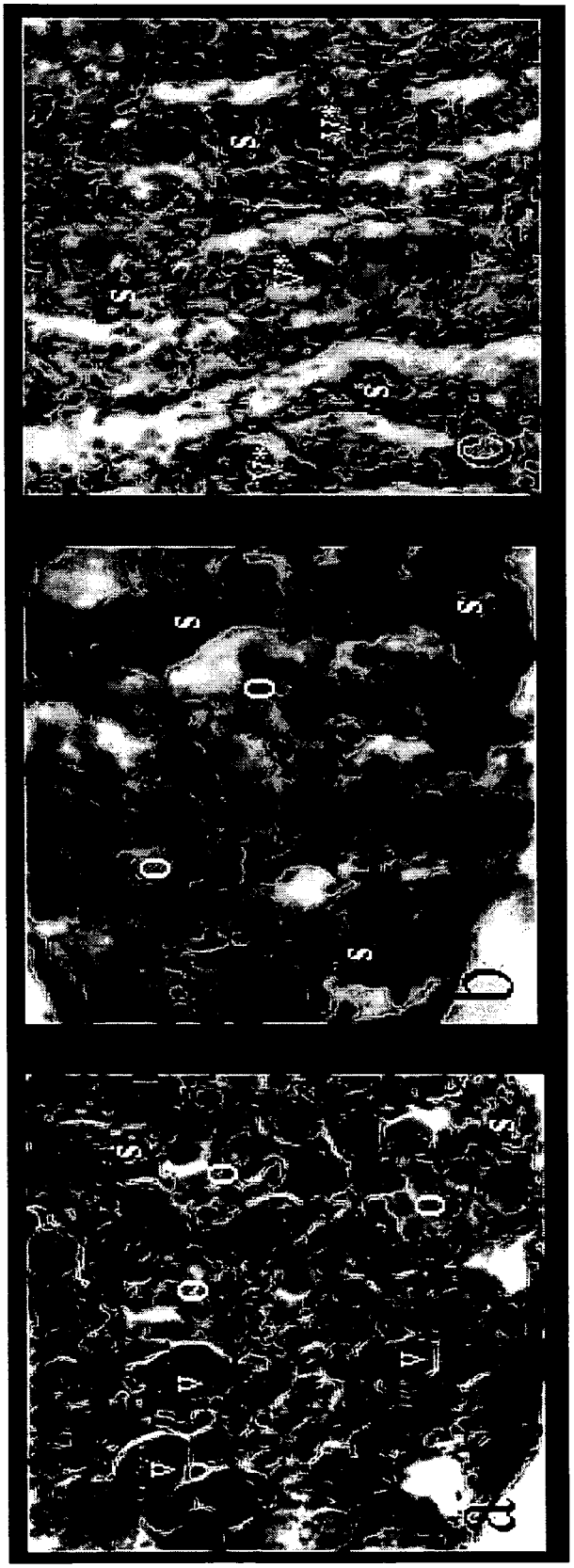
FIGS. 4A. B and C show the effect of GABA-ergic compounds on gonadal development in zebrafish. Hematoxylineosin staining of gonadal tissues of 9-week old zebrafish exposed at 7–10 days pf to A) no treatment, B) 1 mM GABA and C) 100 μM Muscimol. Note greater degree of organization and more advanced gamete development in A), compared to B) and C). s: somatic cells; o: oogonia; v: oocytes in early stages of vitellogenesis; v*: vitellogenic oocytes with abnormal follicle development. A), C) at 200×; B) 400×.

The migration of the GnRH neurons and gonadal development were clearly inhibited by the GABA-ergic treatments. Forebrain GnRH-expressing neurons in the zebrafish arise in the nasal placode and begin migration into the forebrain at 6–10 dpf. Parallel tracts of neurons in untreated larvae can be seen migrating posteriorly along the olfactory tracts in 12 day-old larvae (FIG. 3A). In fish treated at 7–10 dpf, however, GnRH expression is restricted to single paired clusters of neurons in the nasal region (FIGS. 3B and C). No differences are seen in expression patterns of the midbrain cGnRH-II neurons under experimental treatment. In zebrafish, the gonads are formed at 10 dpf, and differentiation of gametogenic cells can be seen at 3 weeks pf (Braat et al., 1999). In our study, a typical structure of an asynchronous ovary (multiple stages of oocytes) can be identified at 9 weeks pf (FIG. 4A). Gonads of zebrafish treated at 7–10 are clearly abnormal in their development as shown in FIGS. 4B and C. The structure of these gonads is disorganized and far less developed. Very few oocytes at early vitellogenic stages are present in these gonads, and somatic tissue occupies most of the tissue mass. This work indicates that GABA-ergic treatments can alter the migration of forebrain GnRH neurons and subsequently suppress gonadal development. Based on the effects of GABA-ergic compounds on the establishment of the GnRH system and gametogenesis in fish, a generic protocol for inducing sterility in finfish has been developed and shown to be effective.

Data on the common model species, zebrafish (*Danio rerio*) and the cultured marine teleost, gilthead seabream (*Sparus aurata*), indicate that the instant process can be successfully used to prevent the functional development of gonads (i.e., ovaries and testes) in fish. Thus, the present invention is an effective sterilization method to inhibit the early establishment of the GnRH system in a broad range of both freshwater and marine species.

The instant disclosure and examples are provided for illustration of the invention and are not intended to limit the scope of the invention. All references are herein incorporated in their entirety by reference.

REFERENCES

Arai, K. 2001. Genetic improvement of aquaculture finfish species by chromosome manipulation techniques in Japan. *Aquaculture* 197:205–228.

Benfey, T. J. and Sutterlin, A. M. 1984. Growth and gonadal development in triploid landlocked Atlantic salmon (*Salmo salar*). *Can. J. Fish. Aquat. Sci.* 41:1387–1392.

Bless E P, Westaway W A, Schwarting G A, Tobet S A 2000 Effects of g-aminobutyric acid (A) receptor manipulation on migrating gonadotropin-releasing hormone neurons through the entire migratory route in vivo and in vitro. *Endocrinology* 141: 1254–1262.

Braat, A. K., Zandbergen, T., Van de Water, S., Goos, H. J. Th., and Zivkovic, D. 1999. Characterization of zebrafish primordial germ cells: morphology and early distribution of vasa RNA. *Dev. Dynamics.* 216:153–167.

Carr, et al., 1997. Occurrence and spawning of cultured Atlantic salmon in Canadian rivers. ICES *J. Marine Science.* 54 (6): 1064–1073.

Galbreath P F, Thorgaard G H 1994 Viability and freshwater performance of Atlantic salmon (*salmo salar*) X brown trout (*Salmo trutta*) triploid hybrids. *Ca J Fish Aquat Sci.*, 5 1 (Suppl. 1): 16–24.

Galbreath P F, Thorgaard G H 1995 Sexual maturation and fertility of diploid and triploid Atlantic salmon X brown trout hybrids. *Aquaculture* 137:299–311.

Johnstone R 1993. Maturity control in Atlantic salmon. In: "Recent advances in aquaculture" (J. F. Muir & R. J. Roberts, eds.) pp. 69–77. Blackwell Scientific Publications. London.

Knibb W. 2000. Genetic improvement of marine fish—which method for industry?. *Aquaculture Res.* 31:11–23.

Naylor, R. A., Goldburg, R. J., Mooney, H., Beveridge, M., Clay, J., Folke, C., Kautsky, N., Lubchenco, J., Primavera, J., and Williams, M. 1998. Natures subsidies to shrimp and salmon farming. *Science* 282: 883–884.

Parhar, I. S., and Sakuma, Y. 1997. Regulation of forebrain and midbrain GnRH neurons in juvenile teleosts. *Fish Physiol. Biochem.* 17:81–84.

Piferrer, F., and Donaldson, E. M. 1993. Sex control in Pacific salmon. In: "Recent advances in aquaculture" (J. F. Muir & R. J. Roberts, eds.) pp. 99–106. Blackwell Scientific Publications. London.

Pauly, D., Christensen, V., Dalsgaard, J., Froese, R., and Torres, F. Jr. 1998. Fishing down marine food webs. *Science* 279: 860–863.

Pauly, D. and Christensen, V. 1995. Primary production required to sustain global fisheries. Nature 374: 255–257.

Safina, C. 1998. The world's imperiled fish. *Scientific American.* P. 58–63.

Sullivan, C. V., Berlinsky, D. L., and Hodson, R. G. 1997. Reproduction. In: Striped Bass and Other Morone Culture. (R. M. Harrel, ed.). pp 11–73. Elsevier Science, New York.

Volpe, et al., 2001. Reproduction of aquacultured Atlantic salmon in Canadian rivers. *Transactions of the American Fisheries Society.* 130 (3): 489–494.

Westerfield M. 1995. The zebrafish book. University of Oregon Press.

White R B, Fernald R D 1998 Ontogeny of gonadotropin-releasing hormone (GnRH) gene expression reveals a distinct origin for GnRH-Containing neurons in the midbrain. *Gen Comp Endo.* 112:322–329.

Wong T-S, Gothilf Y, Meiri 1, Zmora N, Elizur A, Zohar Y 2000 Gene expression of three forms of GnRH at different stages of the gilthead seabream life cycle. 4th International Symposium on Fish Endocrinology, Jul. 31-Aug. 3, 2000 Seattle, Wash.

Zohar, Y., Harel, M., Serfling, S., Stubblefield, J., and Place, A. 2002. U.S. Pat. No. 6,443,097. "A process for farming gilthead seabream and other commercially important marine finfish in recirculating marine aquaculture systems".

Zohar, Y. and Mylonas, C. C. 2001. Endocrine manipulations of spawning in farmed fish: from hormones to genes. *Aquaculture* 197: 99–136.

Zohar, Y. "Compositions and methods for manipulating ovulation and spawning in fish" U.S. Pat. No. 5,288,705.

That which is claimed is:

1. A method of permanently sterilizing fish comprising: administering a compound to an embryonic or juvenile fish that disrupts the establishment of the gonadotropin-releasing hormone system during early development, wherein said compound inhibits migration of GnRH neurons to a hypothalamic locus.

2. The method according to claim 1, wherein the compound comprises gamma aminobutyric acid (GABA) in an effective amount to disrupt the establishment of the gonadotropin-releasing hormone system during early development.

3. The method according to claim 2, wherein the GABA is administered at a daily dose of 25 ug to 400 ug per kg of fish biomass per day for a period of 2–14 days.

4. The method according to claim 2, wherein the GABA is administered at a daily dose of 50 ug to 75 ug per kg of fish biomass per day for a period of 2–4 days.

5. The method according to claim 1, wherein the compound comprises a functional equivalent of gamma aminobutyric acid in an effective amount to disrupt the establishment of the gonadotropin-releasing hormone system during early development.

6. The method according to claim 1, wherein the compound comprises a GABA receptor agonist or a GABA receptor antagonist in an effective amount to disrupt the establishment of the gonadotropin-releasing hormone system during early development.

7. The method of claim 6 wherein the GABA receptor agonist is muscimol.

8. The method according to claim 6, wherein the compound is aminovaleric acid; 3-amino-4-cyclopentane-1-carboxylic acid; muscimol; baclofen, bicuculline; diazepam; topiramate, beta-p-chlorophenyl-GABA; or dehydroepiandrosterone.

9. The method according to claim 6, wherein the GABA, GABA receptor agonist, or GABA receptor antagonist is administered by injection, implantation, dissolving in water wherein the fish are swimming or orally through feed.

10. The method according to claim 1, wherein the fish is seabream or zebrafish.

11. A method to sterilize a fish, the method comprising: administering GABA, GABA receptor agonist, or GABA receptor antagonist to fish larvae in an amount effective to disrupt the establishment of the gonadotropin-releasing hormone system thereby permanently sterilizing the mature fish.

12. The method according to claim 11, wherein the GABA, GABA receptor agonist, or GABA receptor antagonist is administered by injection, implantation, dissolving in water wherein the fish are swimming or orally through feed.

13. A method of permanently sterilizing fish comprising: contacting an embryonic or juvenile fish that is sexually immature with gamma aminobutyric acid (GABA) or a functional equivalent thereof in an effective amount to disrupt the establishment of the gonadotropin-releasing hormone system during early development thereby inhibiting sexual maturity.

14. The method according to claim 13, wherein the GABA functional equivalent is thereof may be selected from the group including aminovaleric acid; 3-amino-4-cyclopentane-1-carboxylic acid; muscimol; baclofen, bicuculline; diazepam; topiramate, beta-p-chlorophenyl-GABA; of dehydroepiandrosterone.

15. The method according to claim 13, wherein the embryonic or juvenile fish is contacted with GABA.

16. The method according to claim 15, wherein the embryonic or juvenile fish was immersed in a concentration of GABA ranging from about $10^{-7}$ to $10^{-3}$ M for a period of time ranging from about 18 hours to about 48 hours.

17. The method according to claim 15, wherein the GABA is administered by injection, implantation, dissolving in water wherein the fish are swimming or orally through feed.

18. The method according to claim 15, where the fish is contacted with GABA at 3 days, 1 week or 2 weeks post fertilization.

* * * * *

UNITED STATES PATENT AND TRADEMARK OFFICE
CERTIFICATE OF CORRECTION

PATENT NO. : 7,194,978 B2 Page 1 of 1
APPLICATION NO. : 10/924001
DATED : March 27, 2007
INVENTOR(S) : Zohar et al.

It is certified that error appears in the above-identified patent and that said Letters Patent is hereby corrected as shown below:

Column 12, line 2 : "dose of 25 ug to 400 ug" should be -- dose of 25 $u$g to 400 $u$g --

Column 12, line 5 : "dose of 50 ug to 75 ug" should be -- dose of 50 $u$g to 75 $u$g --

Signed and Sealed this

Seventeenth Day of July, 2007

JON W. DUDAS
*Director of the United States Patent and Trademark Office*